United States Patent
Kruck et al.

(10) Patent No.: US 12,318,470 B2
(45) Date of Patent: Jun. 3, 2025

(54) AGENT FOR DYEING KERATINUOS MATERIAL, COMPRISING AMINOSILICONE, A CHROMOPHORIC COMPOUND AND AN ADDITION PRODUCT OF $C_1$-$C_6$ ALKYLENE OXIDE(S) TO THE ESTERS OF FATTY ACIDS AND AROMATIC ALCOHOLS

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 48 days.

(21) Appl. No.: 18/251,128

(22) PCT Filed: Oct. 11, 2021

(86) PCT No.: PCT/EP2021/078041
§ 371 (c)(1),
(2) Date: Apr. 28, 2023

(87) PCT Pub. No.: WO2022/096232
PCT Pub. Date: May 12, 2022

(65) Prior Publication Data
US 2023/0398057 A1    Dec. 14, 2023

(30) Foreign Application Priority Data
Nov. 3, 2020 (DE) .......................... 102020213785.4

(51) Int. Cl.
*A61Q 5/10* (2006.01)
*A61K 8/898* (2006.01)
*A61Q 5/06* (2006.01)

(52) U.S. Cl.
CPC ............ *A61K 8/898* (2013.01); *A61Q 5/065* (2013.01); *A61K 2800/432* (2013.01); *A61K 2800/438* (2013.01)

(58) Field of Classification Search
CPC .............. A61K 8/898; A61K 2800/432; A61K 2800/438; A61K 2800/43; A61K 8/39; A61Q 5/065
USPC .......................................................... 8/405
See application file for complete search history.

(56) References Cited

U.S. PATENT DOCUMENTS

2013/0149358 A1    6/2013  Colaco et al.
2020/0170912 A1*   6/2020  Krohn ...................... A61K 8/31

FOREIGN PATENT DOCUMENTS

| CN | 1571765 A | * | 1/2005 | ............ A61Q 15/00 |
| DE | 102008037633 A1 | | 2/2010 | |
| DE | 102018222022 A1 | * | 6/2020 | ............ A61Q 5/10 |
| EP | 2441434 A | | 4/2012 | |
| WO | WO 2017/108828 A1 | * | 6/2017 | ............ A61K 8/411 |

OTHER PUBLICATIONS

STIC Search Report dated Sep. 12, 2024.*
Josh Wood Clour, Database GNPD [Online] MINTEL; Aug. 13, 2020 (Aug. 13, 2020), anonymous: "Gloss Semi-Permanent Treatment Gloss", XP055878859.
Josh Wood Clour, Database GNPD [Online] MINTEL; Jul. 19, 2019 (Jul. 19, 2019), anonymous: "Shade Shot Gloss", XP055878952.
Ims, Vita A. Diamante, Database GNPD [Online] MINTEL; Aug. 4, 2011 (Aug. 4, 2011), anonymous: "Three-Dimensional Shine Hair Tint", XP055878965.

* cited by examiner

*Primary Examiner* — Eisa B Elhilo
(74) *Attorney, Agent, or Firm* — Lorenz & Kopf, LLP

(57) ABSTRACT

An agent for dyeing keratinous material (e.g. human hair) is disclosed. The agent comprises at least one amino-functionalized silicone polymer; at least one color-imparting compound; and at least one addition product of $C_1$-$C_6$ alkylene oxide(s) to the esters of $C_{12}$-$C_{30}$ fatty acids and $C_1$-$C_{12}$ aromatic alcohols. A method for dyeing keratinous material is also disclosed, and comprises applying the agent to keratinous material, exposing the agent to the keratinous material, and rinsing the keratinous material to remove the agent.

17 Claims, No Drawings

AGENT FOR DYEING KERATINUOS MATERIAL, COMPRISING AMINOSILICONE, A CHROMOPHORIC COMPOUND AND AN ADDITION PRODUCT OF $C_1$-$C_6$ ALKYLENE OXIDE(S) TO THE ESTERS OF FATTY ACIDS AND AROMATIC ALCOHOLS

CROSS-REFERENCE TO RELATED APPLICATION

This application is a U.S. National-Stage entry under 35 U.S.C. § 371 based on International Application No. PCT/EP2021/078041, filed Oct. 11, 2021, which was published under PCT Article 21(2) and which claims priority to German Application No. 102020213785.4, filed Nov. 3, 2020, which are all hereby incorporated in their entirety by reference.

TECHNICAL FIELD

The subject of the present application is an agent for coloring keratinous material, in particular human hair, which comprises at least one amino-functionalized silicone polymer (a1), at least one coloring compound (a2) and at least one addition product of $C_1$-$C_6$ alkylene oxide(s) to the esters of fatty acids and aromatic alcohols.

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyes with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user wants particularly long-lasting dyeing, the use of oxidative dyes has so far been his/her only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. For this reason, pigment-based colorants are very much in vogue. However, the color intensities and fastness properties of colorants based on the use of pigments in particular still need to be greatly improved.

It was the task of the present disclosure to provide a coloring agent that enables pigments to be fixed to the hair in an extremely durable manner. When using the agent in a dyeing process, particularly intensive dyeing results should be obtained. Furthermore, dyeing with a good wash fastness, a good leveling capacity and a particularly uniform color result should be achieved. In addition, the abrasion of these pigment colorants should also be particularly low, i.e. the colorants should also have particularly good rub fastness in the event of mechanical contact with clothing or other textiles. In addition, the keratin material, especially the hair, should not feel weighed down or dull or greasy after application of the pigment colorants and should have as pleasant a feel as possible.

Surprisingly, it has now been found that the above problem can be excellently solved if keratinous materials, in particular hair, are colored with an agent comprising at least one amino-functionalized silicone polymer (a1), at least one colorant compound (a2), and at least one addition product of $C_1$-$C_6$ alkylene oxide(s) to the esters of $C_{12}$-$C_{30}$ fatty acids and aromatic $C_1$-$C_{12}$ alcohols (a3).

BRIEF SUMMARY

An agent for dyeing keratinous material (e.g. human hair) is provided. The agent comprises (a1) at least one amino-functionalized silicone polymer; (a2) at least one color-imparting compound; and (a3) at least one addition product of $C_1$-$C_6$ alkylene oxide(s) to the esters of $C_{12}$-$C_{30}$ fatty acids and $C_1$-$C_{12}$ aromatic alcohols.

A method for dyeing keratinous material is also provided. The method comprises: (1) applying the agent to keratinous material; (2) exposing the agent to the keratinous material; and (3) rinsing the keratinous material to remove the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is an agent for coloring keratinous material, in particular human hair, comprising.

(a1) at least one amino-functionalized silicone polymer, and
(a2) at least one color-imparting compound, and
(a3) at least one addition product of $C_1$-$C_6$ alkylene oxide(s) to the esters of $C_{12}$-$C_{30}$ fatty acids and $C_1$-$C_{12}$ aromatic alcohols.

In the course of the work leading to the present disclosure, it has been surprisingly shown that the use of an alkoxylated fatty acid ester (a3) in an agent comprising an amino silicone (a1) as well as a coloring compound (a2) leads to an improvement in color intensity and wash fastness when this agent is applied in a dyeing process on the keratinous material, in particular on human hair. These positive effects were observed in particular when the colorant compound (a2) was a pigment.

Keratinous Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair in particular.

Coloring Agent

The term "coloring agent" is used in the context of the present disclosure for a coloring of the keratin material, in particular of the hair, caused by the use of coloring compounds, in particular pigments. In this coloring process, the pigments are deposited as coloring compounds in a particularly homogeneous, uniform and smooth film on the surface of the keratin material.

The agent as contemplated herein comprises the essential ingredients (a1), (a2) and (a3) preferably in a cosmetic carrier.

Amino-Functionalized Silicone Polymers (a1)

As the first ingredient (a1) essential to the present disclosure, the agent comprises at least one amino-functionalized silicone polymer. The amino-functionalized silicone polymer may alternatively be referred to as amino silicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size, and is partly determined by the polymerization method. For the purposes of the present disclosure, it is preferred if the maximum molecular weight of the silicone polymer is not more than 107 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, dyeing with the best wash fastness were observed when an amino-functionalized silicone polymer (a1) comprising at least one secondary amino group was used in the agent.

In a very particularly preferred embodiment, an agent as contemplated herein is wherein it comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si amino).

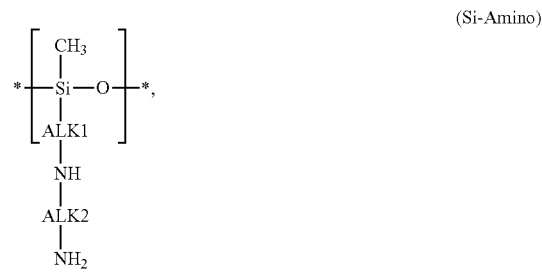

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent as contemplated herein is wherein it comprises at least one amino-functionalized silicone polymer (a1) comprising at least one structural unit of the formula (Si amino),

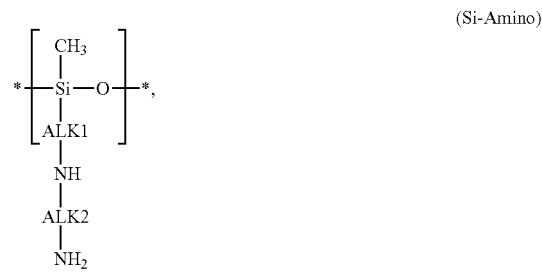

(Si-Amino)

where ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeing with the very best wash fastnesses could be obtained if, in the process as contemplated herein, at least one agent comprising at least one amino-functionalized silicone polymer (a1) comprising structural units of the formula (Si-I) and of the formula (Si-II) was applied to the keratinous material

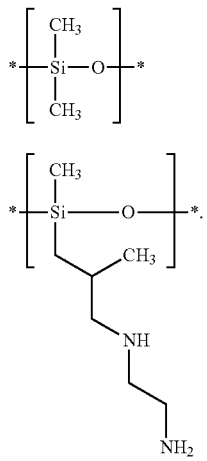

In a further explicitly quite particularly preferred embodiment, an agent as contemplated herein is wherein it comprises at least one amino-functionalized silicone polymer (a1) comprising structural units of the formula (Si-I) and of the formula (Si-II)

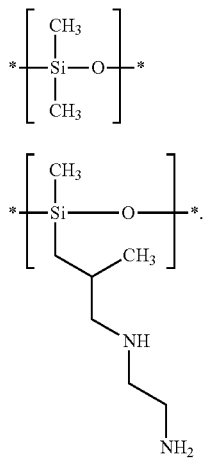

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8. Another amino-functionalized silicone polymer with the structural units (Si-I) and (Si-II) is, for example, the commercial product DOWSIL™ AP-8568 Amino Fluid, which is also commercially marketed by the Dow Chemical Company.

In another preferred embodiment, an agent as contemplated herein is wherein it comprises at least one amino-functional silicone polymer (a1) of the formula of the formula (Si-III),

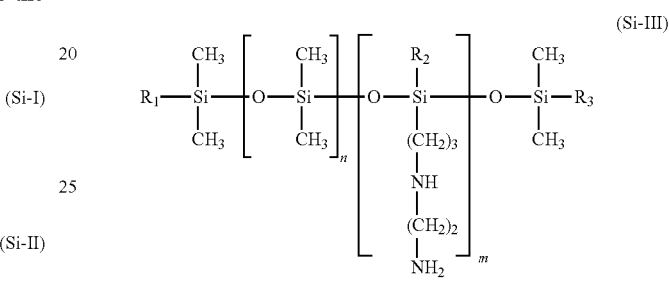

where
  m and n mean numbers chosen so that the sum (n+m) is in the range 1 to 1000,
  n is a number in the range 0 to 999 and m is a number in the range 1 to 1000,
  R1, R2 and R3, which are the same or different, denote a hydroxy group or a $C_{1-4}$ alkoxy group,
  wherein at least one of R1 to R3 represents a hydroxy group.

A further agent preferred as contemplated herein is wherein it comprises at least amino-functional silicone polymer (a1) of the formula of the formula (Si-IV),

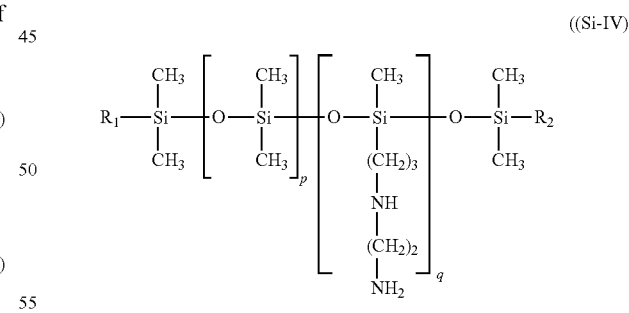

located in the
  p and q mean numbers chosen so that the sum (p+q) is in the range 1 to 1000,
  p is a number in the range 0 to 999 and q is a number in the range 1 to 1000,
  R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si(CH$_3$)$_2$ group is necessarily bonded to an —[O—Si(CH$_3$)$_2$] grouping.

Agents as contemplated herein which contain at least one amino-functional silicone polymer (a1) of the formula of the formula (Si-V) have also proved to be particularly effective with respect to the desired effects:

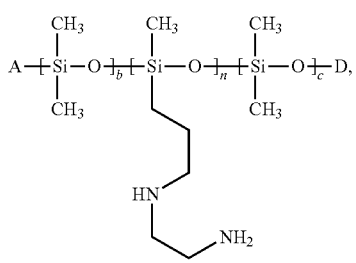

(Si-V)

where

A represents a group —OH, —O—Si(CH$_3$)$_3$, —O—Si(CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, b, n and c stand for integers between 0 and 1000, with the specifications n>0 and b+c>0 at least one of the conditions A=—OH or D=—H is fulfilled.

In the above formula (Si-V), the individual siloxane units are statistically distributed with the indices b, c and n, i.e. they do not necessarily have to be block copolymers.

The agent may further comprise one or more different amino-functionalized silicone polymers represented by the formula (Si-VI)

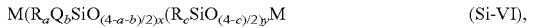

M(R$_a$Q$_b$SiO$_{(4-a-b)/2}$)$_x$(R$_c$SiO$_{(4-c)/2}$)$_y$M    (Si-VI), in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional radical comprising at least one amino functional group. One possible formula for Z is NH(CH$_2$)$_z$NH$_2$, where z is 1 or more. Another possible formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ radical. Another possible formula for Z is —N(CH$_2$)$_z$(CH$_2$)$_{zz}$NX$_2$ or —NX$_2$, wherein each X of X$_2$ is independently selected from the group of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH 2. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, an agent as contemplated herein is wherein it comprises at least one amino-functional silicone polymer of the formula (Si-VII)

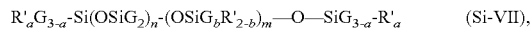

R'$_a$G$_{3-a}$-Si(OSiG$_2$)$_n$-(OSiG$_b$R'$_{2-b}$)$_m$—O—SiG$_{3-a}$-R'$_a$    (Si-VII), wherein:

G is-H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;

a stands for a number between 0 and 3, especially 0;

b stands for a number between 0 and 1, especially 1, m and n are numbers whose sum (m+n) is between 1 and 2000, preferably between 50 and 150, where n preferably assumes values from 0 to 1999 and in particular from 49 to 149 and m preferably assumes values from 1 to 2000, in particular from 1 to 10, R' is a monovalent radical selected from

-Q-N(R")—CH$_2$—CH$_2$—N(R")$_2$

-Q-N(R")$_2$

-Q-N$^+$(R")$_3$A$^-$

-Q-N$^+$H(R")$_2$A$^-$

-Q-N$^+$H$_2$(R")A$^-$

-Q-N(R")—CH$_2$—CH$_2$—N$^+$R"H$_2$A$^-$, where each Q is a chemical bond, —CH₂—, —CH₂—CH₂—, —CH₂CH₂CH₂—, —C(CH₃)₂—, —CH₂CH₂CH₂CH₂—, —CH₂C(CH₃)₂—, —CH(CH₃)CH₂CH₂—, R″ represents identical or different radicals selected from the group of —H, -phenyl, -benzyl, —CH₂—CH(CH₃)Ph, the C$_{1-20}$ alkyl radicals, preferably —CH₃, —CH₂CH₃, —CH₂CH₂CH₃, —CH(CH₃)₂, —CH₂CH₂CH₂H₃, —CH₂CH(CH₃)₂, —CH(CH₃)CH₂CH₃, —C(CH₃)₃, and A represents an anion preferably selected from chloride, bromide, iodide or methosulfate.

In another preferred embodiment, an agent as contemplated herein is exemplified by comprising at least one amino-functional silicone polymer (a1) of the formula (Si-VIIa),

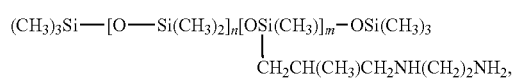
(Si-VIIa)

wherein m and n are numbers whose sum (m+n) is between 1 and 2000, preferably between 50 and 150, n preferably assuming values from 0 to 1999 and in particular from 49 to 149, and m preferably assuming values from 1 to 2000, in particular from 1 to 10.

According to the INCI declaration, these silicones are called trimethylsilylamodimethicones.

In the context of a further preferred embodiment, an agent as contemplated herein is wherein it comprises at least one amino-functional silicone polymer (a1) of the formula (Si-VIIb)

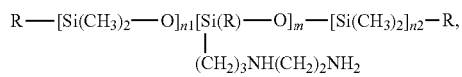
(Si-VIIb)

in which R represents —OH, —O—CH₃ or a —CH₃ group and m, n1 and n2 are numbers whose sum (m+n1+n2) is between 1 and 2000, preferably between 50 and 150, the sum (n1+n2) preferably assuming values from 0 to 1999 and in particular from 49 to 149 and m preferably assuming values from 1 to 2000, in particular from 1 to 10.

According to the INCI declaration, these amino-functionalized silicone polymers are called amodimethicones.

Regardless of which amino-functional silicones are used, agents as contemplated herein comprising an amino-functional silicone polymer whose amine number is above 0.25 meq/g, preferably above 0.3 meq/g and in particular above 0.4 meq/g are preferred. The amine number represents the milliequivalents of amine per gram of the amino-functional silicone. It can be determined by titration and also expressed in the unit mg KOH/g.

Furthermore, agents comprising a special 4-morpholinomethyl-substituted silicone polymer (a1) are also suitable. This amino-functionalized silicone polymer comprises structural units of the formulae (SI-VIII) and of the formula (Si-IX)

(Si-VIII)

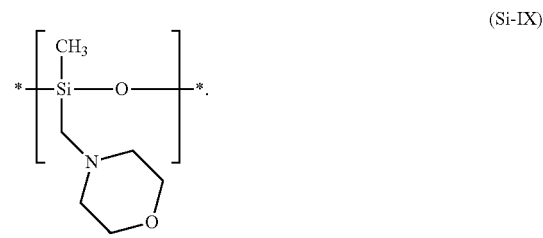
(Si-IX)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

(Si-VIII)

(Si-X)

(Si-IX)

in which

R1 is —CH₃, —OH, —OCH₃, —O—CH₂CH₃, —O—CH₂CH₂CH₃, or —O—CH(CH₃)₂;

R2 is —CH₃, —OH, or —OCH₃.

Particularly preferred compositions as contemplated herein contain at least one 4-morpholinomethyl-substituted silicone of the formula (Si-XI)

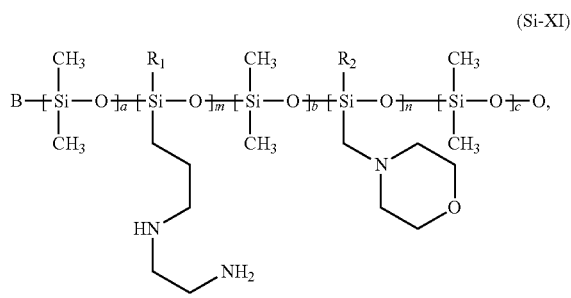

(Si-XI)

wherein

R1 is —CH$_3$, —OH, —OCH$_3$, —O—CH$_2$CH$_3$, —O—CH$_2$CH$_2$CH$_3$, or —O—CH(CH$_3$)$_2$;

R2 is —CH$_3$, —OH, or —OCH$_3$.

B represents a group —OH, —O—Si(CH$_3$)$_3$, —O—Si(CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, a, b and c stand independently for integers between 0 and 1000, with the condition a+b+c>0 m and n independently of each other stand for integers between 1 and 1000 with the proviso that at least one of the conditions B=—OH or D=—H is fulfilled, the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e. the terminal grouping B or D is preferably attached to a dimethylsiloxy grouping. Also in formula (Si-VI), the siloxane units a, b, c, m and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which B=—O—Si(CH$_3$)$_2$OH and D=—Si(CH$_3$)$_3$;
B=—O—Si(CH$_3$)$_2$OH and D=—Si(CH$_3$)$_2$OH;
B=—O—Si(CH$_3$)$_2$OH and D=—Si(CH$_3$)$_2$OCH$_3$;
B=—O—Si(CH$_3$)$_3$ and D=—Si(CH$_3$)$_2$OH; and/or
B=—O—Si(CH$_3$)$_2$OCH$_3$ and D=—Si(CH$_3$)$_2$OH.

The above-listed silicones lead to exorbitant improvements in the hair properties of the hair treated with the agents of the present disclosure, and to a seriously improved protection in oxidative treatment.

It has been found to be particularly advantageous if the agent as contemplated herein comprises the amino-functionalized silicone polymer(s) (a1) in certain quantity ranges. Particularly good results were obtained when the agent included—based on the total weight of the agent—a total amount of from about 0.1 to about 8.0 wt. %, preferably from about 0.2 to about 5.0 wt. %, more preferably from about 0.3 to about 3.0 wt. %, and most preferably from about 0.4 to about 2.5 wt. %.

In another particularly preferred embodiment, an agent as contemplated herein is wherein it comprises—based on the total weight of the agent—one or more amino-functionalized silicone polymers (a1) in a total amount of from about 0.1 to about 8.0 wt. %, preferably from about 0.2 to about 5.0 wt. %, more preferably from about 0.3 to about 3.0 wt. % and very particularly preferably from about 0.4 to about 2.5 wt. %.

Coloring Compounds (a2)

As a second essential component, the composition as contemplated herein comprises at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a composition as contemplated herein is wherein it comprises at least one colorant compound (a2) from the group comprising pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. An agitator is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein is wherein it comprises at least one colorant compound (a2) from the group comprising inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. In particular, preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI 77289), iron blue (ferric ferrocyanides, CI 77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein is wherein it comprises at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein is wherein it comprises (a) at least one colorant compound (a2) from the group of pigments selected from mica- or mica-based pigments which are reacted with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the agent as contemplated herein may also contain one or more colorant compounds (a2) from the group comprising organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein is wherein it comprises at least one colorant compound (a2) from the group of organic pigments which is preferably selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, in particular 14 to 30 µm. The average particle size $D_{50}$, for example, can be determined using dynamic light scattering (DLS).

The colorant compounds (a2), in particular the colorant compounds from the group of pigments, represent the second essential of the agent as contemplated herein and are preferably used in the agent in certain ranges of amounts. Particularly good results were obtained when the agent included—based on the total weight of the agent—one or more pigments (a2) in a total amount of about 0.01 to about 10.0 wt. %, preferably about 0.1 to about 5.0 wt. %, further preferably about 0.2 to about 2.5 wt. % and very preferably about 0.25 to about 1.5 wt. %.

In another very particularly preferred embodiment, an agent as contemplated herein is wherein the agent comprises—based on the total weight of the agent—one or more pigments (a2) in a total amount of from about 0.01 to about 10.0 wt. %, preferably from about 0.1 to about 5.0 wt. %, more preferably from about 0.2 to about 2.5 wt. % and very particularly preferably from about 0.25 to about 1.5 wt. %.

As colorant compounds (a2), the agent as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, a process as contemplated herein is wherein the agent comprises at least one colorant compound (a2) from the group comprising anionic, non-ionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—OO$^-$, —SO$_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In a further embodiment, a process for dyeing keratinous material is wherein the agent comprises at least one anionic direct dye selected from the group of nitrophenylenediamines, the nitroaminophenols, the azo dyes, the anthraquinone dyes, the triarylmethane dyes, the xanthene dyes the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (CI 17200; Fuchsia Red, D&C Red 33, CI 17200), Acid Red 35 (CI C.I.18065), Acid Red 51 (CI 45430, Pyrosin B, Tetraiod-fluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. An agitator is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3 (2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl) benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, an agent as contemplated herein is therefore wherein it comprises at least one direct dye (a2) selected from the group of acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the agents, depending on the desired color intensity. Good results were obtained when the agent comprises—based on the total weight of the agent—one or more direct dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %.

Furthermore, the agent may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the composition—one or more photochromic dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %

Addition Products of $C_1$-$C_6$ Alkylene Oxide(s) to the Esters of $C_{12}$-$C_{30}$ Fatty Acids and $C_1$-$C_{12}$ Aromatic Alcohols (a3)

As a third essential ingredient (a3), the agents as contemplated herein contain at least one addition product of $C_1$-$C_6$ alkylene oxide(s) to the esters of $C_{12}$-$C_{30}$ fatty acids and $C_1$-$C_{12}$ aromatic alcohols.

The addition products of $C_1$-$C_6$ alkylene oxide(s) to the esters of $C_{12}$-$C_{30}$ fatty acids and $C_1$-$C_{12}$ aromatic alcohols (a3) are also abbreviated below as alkoxylated fatty acid esters (a3).

$C_1$-$C_6$-alkylene oxides are the epoxides of $C_1$-$C_6$-alkanes. Particularly well-suited $C_1$-$C_6$ alkylene oxides include ethylene oxide (1,2-epoxyethane), propylene oxide (1,2-epoxypropane) and butylene oxides (1,2-epoxybutane as well as 2,3-epoxybutane).

The ethoxylated fatty acid esters (a3) are based on $C_{12}$-$C_{30}$ fatty acids. These $C_{12}$-$C_{30}$ fatty acids as contemplated herein are linear or branched, saturated or mono- or poly-unsaturated fatty acids, which may also bear one or more hydroxy groups. The $C_{12}$-$C_{24}$ fatty acids as contemplated herein are wherein the comprise 12 to 30 carbon atoms, preferably 12 to 24 carbon atoms. Furthermore, the $C_{12}$-$C_{24}$-fatty acids carry at least one carboxylic acid group.

To form the ethoxylated fatty acid esters (a3) as contemplated herein, for example, one or more fatty acids selected from the group of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselic acid [(Z)-6-octadecenoic acid], palmitoleic acid [(9Z)-hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z, 12Z)-Octadeca-9,12-dienoic acid, Linolenic acid [(9Z,12Z,15Z)-Octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], nervonic acid [(15Z)-tetracos-15-enoic acid] and/or castor oleic acid ((9Z,12R)-12-hydroxy-9-octadecenoic acid.

The ethoxylated fatty acid esters (a3) represent addition products of $C_1$-$C_6$ alkylene oxide(s) to the esters of the previously described $C_{12}$-$C_{24}$ fatty acids and $C_1$-$C_{12}$ aromatic alcohols. Characteristically, the aromatic $C_1$-$C_{12}$ alcohols comprise 1 to 12 carbon atoms and at least one aromatic ring system. The aromatic $C_1$-$C_{12}$ alcohols each have at least one hydroxy group which can either be located directly on the aromatic compound (such as, for example, in the case of phenol) or can be linked to the aromatic compound via an aliphatic unit (such as, for example, in the case of benzyl alcohol or 2-phenoxyethanol). The structures of the aromatic $C_1$-$C_{12}$ alcohols may also comprise further heteroatoms, such as oxygen or nitrogen.

The corresponding aromatic $C_1$-$C_{12}$ alcohols can be monohydric or polyhydric alcohols, i.e. the alcohols can have one or more hydroxyl groups.

Monohydric aromatic $C_1$-$C_{12}$ alcohols are very particularly preferred. This class of compounds comprises exactly one hydroxy group. Suitable representatives include phenol, benzyl alcohol, 2-phenylethyl alcohol and 2-phenoxyethanol.

Accordingly, an agent for dyeing keratinous material, in particular human hair, is particularly preferred, comprising
(a1) at least one amino-functionalized silicone polymer, and
(a2) at least one color-imparting compound, and
(a3) at least one addition product of $C_1$-$C_6$ alkylene oxide(s) to the esters of $C_{12}$-$C_{30}$ fatty acids and $C_1$-$C_{12}$ monohydric aromatic alcohols.

Particularly good wash fastness properties and rub fastness properties could be obtained if at least one adducts (a3) of $C_1$-$C_6$ alkylene oxide(s) was used in the agent as contemplated herein on an ester which is obtained by esterification of a $C_{12}$-$C_{30}$ fatty acid with an aromatic $C_1$-$C_{12}$ alcohol from the group comprising benzyl alcohol, phenol, 2-phenylethyl alcohol and 2-phenoxyethanol.

In the context of a further preferred embodiment, an agent as contemplated herein is wherein it comprises:
(a3) at least one addition product of $C_1$-$C_6$ alkylene oxide(s) to an ester obtained by esterification of a $C_{12}$-$C_{24}$ fatty acid with a $C_1$-$C_{12}$ aromatic alcohol selected from the group of benzyl alcohol, phenol, 2-phenylethyl alcohol and 2-phenoxyethanol, very preferably benzyl alcohol.

Within the scope of a particularly preferred embodiment, a means as contemplated herein is wherein it comprises at least one addition product (a3) of $C_1$-$C_6$ alkylene oxide(s) to an ester obtained by esterification of a $C_{12}$-$C_{24}$ fatty acid with benzyl alcohol.

In the context of a further preferred embodiment, an agent as contemplated herein is wherein it comprises at least one addition product (a3) of ethylene oxide and/or propylene oxide to an ester obtained by esterification of a $C_{12}$-$C_{24}$ fatty acid with a $C_1$-$C_{12}$ aromatic alcohol selected from the group of benzyl alcohol, phenol, 2-phenylethyl alcohol and 2-phenoxyethanol.

In the context of a further particularly preferred embodiment, an agent as contemplated herein is wherein it comprises at least one addition product (a3) of ethylene oxide and/or propylene oxide to an ester obtained by esterification of a $C_{12}$-$C_{24}$ fatty acid with benzyl alcohol.

As previously described, particularly well-suited $C_1$-$C_6$ alkylene oxides include ethylene oxide (1,2-epoxyethane), propylene oxide (1,2-epoxypropane) and butylene oxides (1,2-epoxybutane and 2,3-epoxybutane). Ethylene oxide (1,2-epoxyethane) and propylene oxide (1,2-epoxypropane)

are explicitly very particularly preferred. Propylene oxide (1,2-epoxypropane) is the most preferred.

A corresponding addition product of ethylene oxide to the esters of $C_{12}$-$C_{30}$ fatty acids and aromatic $C_1$-$C_{12}$ alcohols (a3) is formed when the $C_{12}$-$C_{30}$ fatty acid itself or the ester already formed from it is reacted with ethylene oxide (alternatively 1,2-epoxyethane, CAS number 75-21-8).

Similarly, a corresponding addition product of propylene oxide to the esters of $C_{12}$-$C_{30}$ fatty acids and $C_1$-$C_{12}$ aromatic alcohols (a3) is formed when the $C_{12}$-$C_{30}$ fatty acid itself or the ester already formed from it is reacted with propylene oxide (alternative name 1,2-epoxypropane, CAS numbers 75-56-9 (racemate), 15448-47-2 ((R)-enantiomer, 16088-62-3 (S)-enantiomer).

If the $C_{12}$-$C_{30}$ fatty acid itself is reacted with ethylene oxide, an adduct may first form starting from the carboxylic acid moiety of the $C_{12}$-$C_{30}$ fatty acid and the ethylene oxide, forming a moiety *—C(O)—O—CH$_2$—CH$_2$—O—*. This grouping is also an ester. If one mole of ethylene oxide is reacted per mole of fatty acid, a simple adduct with one unit of *—CH$_2$—CH$_2$—O—* is formed on average. However, depending on the molar excess of ethylene oxide used, multiple adducts can also form, with several units of *—CH$_2$—CH$_2$—O—* present per mole of $C_{12}$-$C_{30}$ fatty acid. To form the ester (a3), this adduct is then further reacted with at least one aromatic $C_1$-$C_{12}$ alcohol. The positions marked with an asterisk here represent the bond to the remaining part of the fatty acid and the bond with the remaining part of the alcohol.

If the $C_{12}$-$C_{30}$ fatty acid is reacted analogously with propylene oxide, an adduct may first form starting from the carboxylic acid grouping of the $C_{12}$-$C_{30}$ fatty acid and the propylene oxide, so that a grouping *—C(O)—O—CH(CH$_3$)—CH$_2$—O—* or a grouping *—C(O)—O—CH$_2$—CH(CH$_3$)—O—*. A mixture of the two aforementioned groupings is usually obtained in the reaction mixture. Both groupings are also esters. If one mole of propylene oxide is reacted per mole of fatty acid, a simple adduct with a mixture of the units *—CH(CH$_3$)—CH$_2$—O—* and *—CH$_2$—CH(CH$_3$)—O—* is formed on average. Depending on the molar excess of propylene oxide used, however, multiple adducts can also form, with several units of *—CH(CH$_3$)—CH$_2$—O—* and/or *—CH$_2$—CH(CH$_3$)—O—* then being present per mole of $C_{12}$-$C_{30}$ fatty acid. To form the ester (a3), this adduct is then further reacted with at least one aromatic $C_1$-$C_{12}$ alcohol. The positions marked with an asterisk here represent the bond to the remaining part of the fatty acid and the bond with the remaining part of the alcohol.

Furthermore, it is in principle conceivable for the $C_{12}$-$C_{30}$ fatty acid to be reacted with a mixture of ethylene oxide and propylene oxide. In this case, mixtures of the adducts described above are formed. The reactions of higher alkylene oxides, such as, for example, butylene oxides, are also possible in this way with the $C_{12}$-$C_{30}$ fatty acids.

The addition products prepared in this way lead, for example, to the alkoxylated fatty acid esters of the general formula (AFE-I)

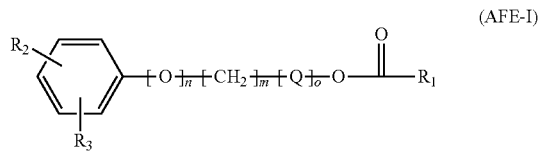
(AFE-I)

where
R1 represents a saturated or unsaturated $C_{11}$-$C_{29}$ alkyl group
R2, R3 independently represent a hydrogen atom, a $C_1$-$C_6$ alkyl group, a hydroxy group or a
$C_1$-$C_6$ alkoxy group,
n represents the number 0 or 1,
m represents an integer from 0 to 6,
represents an integer from 1 to 60, and
Q represents a structural unit —O—CH$_2$—CH$_2$—, —O—CH(CH$_3$)—CH$_2$— or —O—CH$_2$—CH(CH$_3$)—, with the proviso that if m is 0, then n is also 0.

With agents comprising at least ethoxylated fatty acid ester (a3) of formula (AFE-I), dyeing was obtained which were particularly distinguished in terms of good wash fastness and good rub fastness. For this reason, the use of one or more ethoxylated fatty acid esters (a3) of formula (AFE-I) in the agents as contemplated herein is particularly preferred.

In the context of a further particularly preferred embodiment, an agent as contemplated herein is wherein it comprises
(a3) at least one alkoxylated fatty acid ester of the general formula (AFE-I)

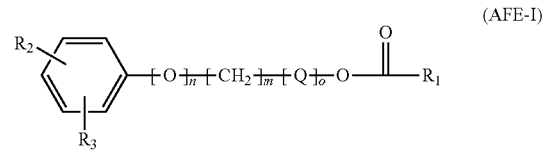
(AFE-I)

where
R1 represents a saturated or unsaturated $C_{11}$-$C_{29}$ alkyl group
R2, R3 independently represent a hydrogen atom, a $C_1$-$C_6$ alkyl group, a hydroxy group or a
$C_1$-$C_6$ alkoxy group,
n represents the number 0 or 1,
m represents an integer from 0 to 6,
represents an integer from 1 to 60, and
Q represents a structural unit —O—CH$_2$—CH$_2$—, —O—CH(CH$_3$)—CH$_2$— or —O—CH$_2$—CH(CH$_3$)—, with the proviso that if m is 0, then n is also 0.

The R1 radical represents a saturated or unsaturated $C_{11}$-$C_{29}$ alkyl group. A $C_{11}$-$C_{23}$ unsaturated alkyl group may comprise one or more double bonds and is alternatively referred to as a $C_{11}$-$C_{23}$ unsaturated alkenyl group. The saturated or unsaturated $C_{11}$-$C_{29}$ alkyl group may be linear or branched.

Preferably, R1 represents a linear, saturated or unsaturated $C_{11}$-$C_{23}$ alkyl group.

R2 and R3 represent, from each other, a hydrogen atom, a $C_1$-$C_6$ alkyl group, a hydroxy group or a $C_1$-$C_6$ alkoxy group. Very preferably, R2 and R3 both represent a hydrogen atom.

The index number n stands for the number 0 or 1. Preferably, n stands for the number 0.

The index number m stands for an integer from 0 to 6. Preferably, m stands for the number 1.

The index number o stands for an integer from 1 to 60. Preferably, o is an integer from 1 to 30, more preferably from 1 to 20, still more preferably from 1 to 10, and most preferably from 1 to 5.

The radical Q stands for a structural unit —O—CH$_2$—CH$_2$—, —O—CH(CH$_3$)—CH$_2$— or —O—CH$_2$—CH(CH$_3$)—. Particularly preferably, Q represents a structural unit —O—CH(CH$_3$)—CH$_2$— or —O—CH$_2$—CH(CH$_3$)—.

When o is a number greater than 1, the compounds of formula (AFE-I) (or also of formula (AFE-II)) contain multiple structural units Q, in which case each structural unit Q can be selected independently of the other structural units Q.

Accordingly, a preferred agent as contemplated herein is wherein it comprises.
(a3) at least one alkoxylated fatty acid ester of the general formula (AFE-I)

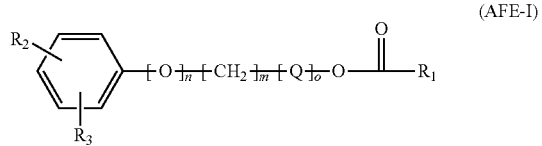

where
R1 represents a saturated or unsaturated C$_{11}$-C$_{29}$ alkyl group
R2, R3 independently represent a hydrogen atom, a C$_1$-C$_6$ alkyl group, a hydroxy group or a C$_1$-C$_6$ alkoxy group,
n represents the number 0 or 1,
m represents an integer from 0 to 6,
represents an integer from 1 to 60, and
Q represents a structural unit —O—CH$_2$—CH$_2$—, —O—CH(CH$_3$)—CH$_2$— or —O—CH$_2$—CH(CH$_3$)—, with the proviso that if m is 0, then n is also 0,
and where, in the case of o greater than 1, each structural unit Q can be chosen independently of the other structural units Q.

In summary, particularly good results were obtained with the agents as contemplated herein, which comprises
(a3) at least one alkoxylated fatty acid ester of the general formula (AFE-I),

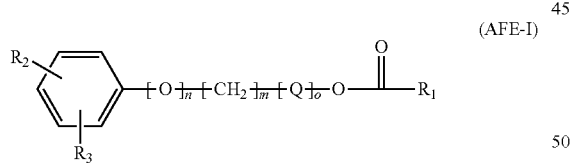

where
R1 represents a saturated or unsaturated C$_{11}$-C$_{29}$ alkyl group
R2, R3 both stand for a hydrogen atom,
n stands for the number 0,
m stands for the number 1,
is an integer from 1 to 30, preferably from 1 to 20, more preferably from 1 to 10, and most preferably from 1 to 5, and
Q is a structural unit —O—CH(CH$_3$)—CH$_2$— or —O—CH$_2$—CH(CH$_3$)—.

In the context of a further very particularly preferred embodiment, an agent as contemplated herein is wherein it
(a3) at least one alkoxylated fatty acid ester of the general formula (AFE-I)

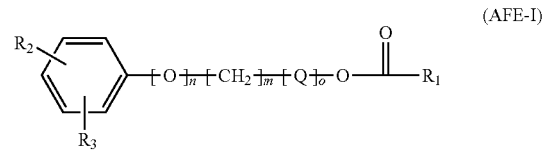

where
R1 represents a saturated or unsaturated C$_{11}$-C$_{29}$ alkyl group
R2, R3 both stand for a hydrogen atom,
n stands for the number 0,
m stands for the number 1,
is an integer from 1 to 30, preferably from 1 to 20, more preferably from 1 to 10, and most preferably from 1 to 5, and
Q is a structural unit —O—CH(CH$_3$)—CH$_2$— or —O—CH$_2$—CH(CH$_3$)—.

The very particularly preferred alkoxylated fatty acid esters of this embodiment also fall under the general formula (AFE-II)

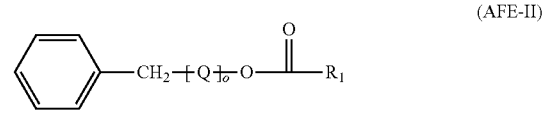

where
R1 represents a saturated or unsaturated C$_{11}$-C$_{29}$ alkyl group
is an integer from 1 to 30, preferably from 1 to 20, more preferably from 1 to 10, and most preferably from 1 to 5, and
Q is a structural unit —O—CH(CH$_3$)—CH$_2$— or —O—CH$_2$—CH(CH$_3$)—.

In the context of a further very particularly preferred embodiment, an agent as contemplated herein is wherein it
(a3) comprises at least one alkoxylated fatty acid ester of the general formula (AFE-II)

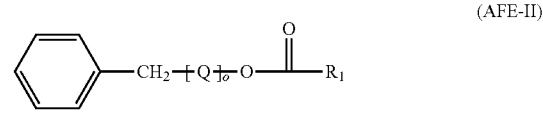

where
R1 represents a saturated or unsaturated C$_{11}$-C$_{29}$ alkyl group
is an integer from 1 to 30, preferably from 1 to 20, more preferably from 1 to 10, and most preferably from 1 to 5, and
Q is a structural unit —O—CH(CH$_3$)—CH$_2$— or —O—CH$_2$—CH(CH$_3$)—.

Again, in the case of o greater than 1, each structural unit Q can be chosen independently of the other structural units Q.

In the alkoxylated fatty acid esters of the general formula (AFE-II), the structural units Q are aligned in such a way that the oxygen atom is located in the grouping —O—CH(CH$_3$)—CH$_2$— and/or. —O—CH$_2$—CH(CH$_3$)— is adjacent to the benzyl group, and the respective unit —CH$_2$— or —CH(CH$_3$)— is adjacent to the ester group —O—C(O)—R1.

One explicitly quite particularly suitable compound of this type is PPG-3 benzyl ether myristate, which is also known alternatively as α-(1-oxotetradecyl)-ω-(phenylmethoxy) poly[oxy(methyl-1,2-ethanediyl)] and bears CAS number 642443-86-5.

PPG-3 Benzyl Ether Myristate can be purchased, for example, under the trade name Crodamol STS from the company Croda.

In the context of a further very particularly preferred embodiment, an agent as contemplated herein is wherein it
(a3) comprises PPG-3 Benzyl Ether Myristate.

Further type of adducts of ethylene oxide with the esters of $C_{12}$-$C_{30}$ fatty acids and aromatic $C_1$-$C_{12}$ alcohols (a3) is present when an ester with a $C_1$-$C_6$ alkylene oxide said ester being obtained by esterifying a $C_{12}$-$C_{30}$ fatty acid having at least one hydroxy group with a $C_1$-$C_{12}$ aromatic alcohol. For example, castor oleic acid ((9Z,12R)-12-hydroxy-9-octadecenoic acid) can first be esterified with benzyl alcohol, phenol, 2-phenylethyl alcohol, or 2-phenoxyethanol. When these adducts are formed, the $C_1$-$C_6$ alkylene oxide or oxides are then attached to the hydroxyl group of the castor oil acid.

If one mole of $C_1$-$C_6$ alkylene oxide is reacted per mole of fatty acid, then, if ethylene oxide is used, for example, as the alkylene oxide, one unit *—$CH_2$—$CH_2$—O—* can be added to the hydroxyl group of the castor oil acid. However, depending on the molar excess of ethylene oxide used, multiple adducts can also be formed, with several units of *—$CH_2$—$CH_2$—O—* added to each hydroxyl group of the fatty acid, and/or with several units of *—$CH_2$—$CH_2$—O—* also added to each free hydroxyl group of the glycerol. These addition products of $C_1$-$C_6$ alkylene oxide(s) to the esters of $C_{12}$-$C_{30}$ fatty acids and $C_1$-$C_{12}$ aromatic alcohols are also as contemplated herein.

The alkoxylated fatty acid esters (a3) are particularly preferred in certain ranges of amounts in the agent as contemplated herein.

Particularly good results were obtained when the agent included—based on the total weight of the agent—one or more alkoxylated fatty acid esters (a3) in a total amount of from 0.1 to 20.0 wt. %, preferably from 0.5 to 15.0 wt. %, more preferably from 1.0 to 10.0 wt. %, still more preferably from 1.0 to 6.0 wt. % and most preferably from 1.0 to 1.8 wt. %.

Within the scope of a further preferred embodiment, an agent as contemplated herein is wherein it comprises—based on the total weight of the agent—one or more alkoxylated fatty acid esters (a3) in a total amount of from 0.1 to 20.0 wt. %, preferably from 0.5 to 15.0 wt. %, more preferably from 1.0 to 10.0 wt. %, still more preferably from 1.0 to 6.0 wt. % and very particularly preferably from 1.0 to 1.8 wt. %.

In the work leading to the present disclosure, it has been found that the presence of one or more of the previously described alkoxylated fatty acid esters (a3) optimally disperses the coloring compounds (a2), especially when these are pigments, in the agent as contemplated herein. It is assumed that the pigments dispersed particularly finely in the agent in this way can be applied very evenly and in the form of a fine, resistant film to the keratin material, which means that the rub fastness properties of the colorations obtained in this way are particularly good. Furthermore, it is assumed that this particularly fine dispersion of the pigments in the agent is also responsible for the good wash fastness properties that can be achieved with the agents as contemplated herein.

Thus, very good results were obtained when the alkoxylated fatty acid ester(s) (a3) were included as the major dispersing aids or additives in the agent of the present disclosure. Further work has also shown that this effect can be further enhanced if a further $C_1$-$C_6$ alkylene oxide addition product (a4) is added to the compositions.

Addition Products of $C_1$-$C_6$ Alkylene Oxide(s) to Aliphatic $C_1$-$C_{24}$ Alkanols (a4)

The substance group (a4) that is particularly effective as a further dispersing additive is the addition products of $C_1$-$C_6$ alkylene oxides to $C_1$-$C_{24}$ alkanols.

In the following, the addition products of $C_1$-$C_6$ alkylene oxide(s) to aliphatic $C_1$-$C_{24}$ alkanols (a4) are also referred to in abbreviated form as alkoxylated alkanols.

Within the scope of a further particularly preferred embodiment, an agent as contemplated herein is therefore further wherein it comprises
a4) at least one Addition products of $C_1$-$C_6$ alkylene oxide(s) to aliphatic $C_1$-$C_{24}$ alkanols (a4)

$C_1$-$C_6$ alkylene oxides suitable as contemplated herein and their preferred and particularly preferred representatives have already been defined in the preceding sections.

As contemplated herein, the $C_1$-$C_{24}$ alkanols are compounds having 1 to 14 carbon atoms and a hydroxy group. Examples which may be mentioned are methanol, ethanol, 1-propanol, 2-propanol, 1-butanol, 2-butanol, 1-pentanol, 2-pentanol, 3-pentanol, 1-hexanol, 2-hexanol, 3-hexanol, 1-Heptanol, 2-heptanol, 3-heptanol, 4-Heptanol, 1-octanol, 2-octanol, 3-octanol, 4-octanol, 1-nonanol, 2-nonanol, 3-nonanol, 4-nonanol, 5-nonanol, 1-decanol, 2-decanol, 3-decanol, 4-decanol, 5-decanol, 1-undecanol, 2-undecanol, 3-Undecanol, 4-undecanol, 5-Undecanol, 6-undecanol, 1-dodecanol, 2-dodecanol, 3-dodecanol, 4-dodecanol, 5-dodecanol, 6-dodecanol, 1-tridecanol, 2-tridecanol, 3-Tridecanol, 4-Tridecanol, 5-Tridecanol, 6-Tridecanol, 7-Tridecanol, 1-Tetradecanol, 2-Tetradecanol, 3-Tetradecanol, 4-Tetradecanol, 5-Tetradecanol, 6-Tetradecanol, 7-Tetradecanol, 1-pentadecanol, 2-pentadecanol, 3-pentadecanol, 4-pentadecanol, 5-pentadecanol, 6-pentadecanol, 7-pentadecanol, 8-pentadecanol, 1-hexadecanol, 2-hexadecanol, 3-hexadecanol, 4-hexadecanol, 5-hexadecanol, 6-Hexadecanol, 7-Hexadecanol, 8-Hexadecanol, 1-Heptadecanol, 2-heptadecanol, 3-Heptadecanol, 4-Heptadecanol, 5-Heptadecanol, 6-Heptadecanol, 7-Heptadecanol, 8-heptadecanol, 1-octadecanol, 2-octadecanol, 3-octadecanol, 4-octadecanol, 5-octadecanol, 6-Octadecanol, 7-Octadecanol, 8-octadecanol and 9-octadecanol.

Particularly well-suited addition products of $C_1$-$C_6$ alkylene oxide(s) to aliphatic $C_1$-$C_{24}$ alkanols (a4) are the compounds of the general formula (AA-I)

(AA-I)

wherein
R4 represents a saturated or unsaturated $C_1$-$C_{24}$ alkyl group, and
P represents a structural unit —O—$CH_2$—$CH_2$—, —O—CH($CH_3$)—$CH_2$— or —O—$CH_2$—CH($CH_3$)—,
and
s represents an integer from 1 to 60.

The radical R4 represents a saturated or unsaturated, $C_1$-$C_{24}$ alkyl group. The residues R4 can be unsaturated from a carbon number of at least 2 C atoms. An unsaturated $C_2$-$C_{24}$ alkyl group may comprise one or more double bonds and is alternatively referred to as a $C_2$-$C_{24}$ alkenyl group. The saturated or unsaturated $C_1$-$C_{24}$ alkyl group may be linear or branched.

Particularly preferably, the R4 radical represents a saturated, unbranched $C_1$-$C_{12}$ alkyl group. In particular, the rest R4 stands for a saturated, unbranched $C_1$-$C_6$ alkyl group.

In the compounds of formula (AA-I), P represents a structural unit —O—$CH_2$—$CH_2$—, —O—$CH(CH_3)$—$CH_2$— or —O—$CH_2$—$CH(CH_3)$—. The number of structural units included in the compounds of the formula (AA-I) is determined by the index s. In this case, the structural units P are oriented in such a way that the oxygen atom in each group —O—$CH_2$—$CH_2$—, —O—$CH(CH_3)$—$CH_2$— and —O—$CH_2$—$CH(CH_3)$— is located adjacent to the alkyl radical R 4, and the respective unit —$CH_2$— or —$CH(CH_3)$- is adjacent to the hydroxy group —OH.

When s is a number greater than 1, multiple structural units P are present in the compounds of formula (AA-I). In this case, each structural unit P can be chosen independently from the other structural units P.

The index number s represents an integer from 1 to 60, preferably an integer from 1 to 40, further preferably an integer from 10 to 30, and most preferably an integer from 10 to 20.

Within the scope of a further particularly preferred embodiment, an agent as contemplated herein is therefore further wherein it comprises (a4) at least one addition product of $C_1$-$C_6$-alkylene oxide(s) to aliphatic $C_1$-$C_{24}$-alkanols of the formula (AA-I),

(AA-I)

wherein

R4 represents a saturated or unsaturated $C_1$-$C_{24}$ alkyl group, preferably a $C_1$-$C_{12}$ alkyl group, particularly preferably a $C_1$-$C_6$ alkyl group, and P represents a structural unit —O—$CH_2$—$CH_2$—, —O—$CH(CH_3)$—$CH_2$— or —O—$CH_2$—$CH(CH_3)$—, and s is an integer from 1 to 60, preferably an integer from 1 to 40, more preferably an integer from 10 to 30, and most preferably an integer from 10 to 20.

A very particularly suitable adduct of $C_1$-$C_6$ alkylene oxide(s) with aliphatic $C_1$-$C_{24}$ alkanols of the formula (AA-I) is propylene glycol monobutyl ether, which is also referred to as PPG-14 butyl ether, and the CAS number 9003-13-8. PPG-14 butyl ether can be purchased commercially under the trade name Ucon Fluid AP from Dow.

Within the scope of a further particularly preferred embodiment, an agent as contemplated herein is therefore further wherein it comprises (a4) PPG-14 Butyl ether.

The alkoxylated alkanols (a4) are particularly preferred in certain ranges of amounts in the agent as contemplated herein.

Particularly good results were obtained when the agent included—based on the total weight of the agent—one or more alkoxylated alkanols (a4) in a total amount of 0.1 to 20.0 wt. %, preferably 0.2 to 15.0 wt. %, more preferably 0.3 to 10.0 wt. %, still more preferably 0.4 to 5.0 wt. % and most preferably 0.5 to 3.0 wt. %.

Within the scope of a further preferred embodiment, an agent as contemplated herein is
wherein it comprises—based on the total weight of the agent—one or more addition products of $C_1$-$C_6$ alkylene oxide(s) to aliphatic $C_1$-$C_{24}$ alkanols (a4) in a total amount of 0.1 to 20.0 wt. %, preferably 0.2 to 15.0 wt. %, more preferably from 0.3 to 10.0 wt. %, even more preferably from 0.4 to 5.0 wt. %, even more preferably from 0.5 to 3.0 wt. % and most preferably from 0.5 to 1.5 wt.

Agent pH Value

The pH value of the agent as contemplated herein is preferably adjusted to a slightly acidic to alkaline pH value. Most preferably, the agent has an alkaline pH in the range of from about 3.8 to 11.5, preferably from about 4.0 to about 10.0, and further preferably from about 5.0 to about 9.0 and most preferably from about 6.0 to about 8.0

Within the scope of a further particularly preferred embodiment, The Agent it comprises water and has a pH of from 3.8 to 11.5 preferably from 4.0 to 10.0, more preferably from 5.0 to 9.0 and most preferably from 6.0 to 8.0.

To adjust the desired pH, the agent as contemplated herein may contain at least one acidifying agent and/or alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore wherein the agent as contemplated herein comprises an alkanolamine selected from 2-aminoethan-1-ol and/or 2-amino-2-methylpropan-1-ol as alkalizing agent.

For the purposes of the present disclosure, an amino acid is an organic compound comprising at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore wherein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is wherein the colorant comprises at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, omithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

To adjust the desired pH, the agent as contemplated herein may also contain at least one buffer system comprising at least one inorganic or organic acid and at least one salt of this acid.

A particularly well-suited inorganic acid is potassium dihydrogen phosphate. Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of 4.4.

Another particularly suitable inorganic acid (b2-I) is sodium dihydrogen phosphate. Sodium dihydrogen phosphate has the molecular formula $NaH_2PO_4$ and carries the CAS numbers 7558-80-7 (anhydrate), 10049-21-5 (monohdate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as a corresponding salt of the above two acids is dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids (b2-II) is disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Other Optional Formulation Ingredients in the Agent

In addition to the ingredients (a1), (a2), (a3) and, if appropriate, (a4) which are essential to the present disclosure or particularly preferred, as already described, the agent may also contain further optional ingredients.

As a further optional ingredient, the agent as contemplated herein may also additionally comprise at least one fat ingredient. Suitable fat ingredients can be selected from the group of $C_{12}$-$C_{24}$ fatty alcohols, $C_{12}$-$C_{24}$ fatty acid triglycerides, $C_{12}$-$C_{24}$ fatty acid monoglycerides, $C_{12}$-$C_{24}$ fatty acid diglycerides and/or hydrocarbons.

The $C_{12}$-$C_{24}$ fatty alcohols can be saturated, mono- or polyunsaturated, linear or branched fatty alcohols with 12 to 24 C atoms.

Examples of preferred linear, saturated $C_{12}$-$C_{24}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol. It has been found to be quite preferable to use one or more $C_{12}$-$C_{24}$ fatty alcohols in quite specific ranges of amounts.

It is particularly preferred if the agent comprises one or more $C_{12}$-$C_{24}$ fatty alcohols in a total amount—based on the total weight of the agent of from 2.0 to 50.0 wt. %, preferably from 3.0 to 30.0 wt. %, more preferably from 4.0 to 20.0 wt. %, still more preferably from 5.0 to 15.0 wt. %, and most preferably from 5.0 to 10.0 wt. %.

Furthermore, the agent may also contain at least one preservative. The following substances and their mixtures can be used as preservatives:

aromatic alcohols, such as phenoxyethanol, benzyl alcohol, phenethyl alcohol, phenoxy isopropanol, Aldehydes such as formaldehyde solution and paraformaldehyde, glutaraldehyde Parabens, for example methylparaben, ethyl paraben, propylparaben, butylparaben, isobutyl paraben 1,2-alkanediols with 5 to 22 carbon atoms in the carbon chain, such as 1,2-pentanediol, 1,2-hexanediol, 1,2-heptanediol, 1,2-decanediol, 1,2-dodecanediol, 1,2-hexadecanediol, Formaldehyde-releasing compounds, such as DMDM hydantoin, diazolidinyl urea Halogenated compounds such as isothiazolinones, such as methylchloroisothiazolinone/methylisothiazolinones, triclosan, triclocarban, iodopropynyl butylcarbamate, 5-bromo-5-nitro-1,3-dioxane, chlorhexidine digluconate and chlorhexidine acetate, 2-bromo-2-nitropropane-1,3-diol, methyl dibromoglutaronitrile, Inorganic compounds such as sulfites, boric acid and borates, bisulfites, Cationic substances such as quaternium-15, benzalkonium chloride, benzethonium chloride, polyaminopropyl biguanide, Organic acids and their physiologically compatible salts, such as citric acid, lactic acid, acetic acid, benzoic acid, sorbic acid, salicylic acid, dehydroacetic acid Active ingredients with additional effects such as zinc pyrithione, piroctonolamine, Antioxidants such as BHT (butylated hydroxytoluene), BHA (butylated hydroxyanisole), propyl gallate, t-butylhydroquinone, Complexing agents such as EDTA and its derivatives, HEDTA and its derivatives, etidronic acid and its salts.

If required, the agents as contemplated herein may also additionally contain at least one surface-active substance, such surface-active substances being referred to as surfactants or as emulsifiers, depending on the field of application: They are preferably selected from anionic, cationic, zwitterionic, amphoteric and non-ionic surfactants and emulsifiers.

Preferred anionic surfactants are fatty acids, alkyl sulphates, alkyl ether sulphates and ether carboxylic acids with 10 to 20 C atoms in the alkyl group and up to 16 glycol ether groups in the molecule. The anionic surfactants are used in amounts of 0.1 to 45 wt. %, preferably 1 to 30 wt. % and very preferably 1 to 15 wt. %, based on the total amount of the agent ready for use.

Preferred zwitterionic surfactants are betaines, N-Alkyl-N,N-dimethylammonium glycinate, N-Acyl aminopropyl-N,N-dimethylammonium glycinate, and 2-Alkyl-3-carboxymethyl-3-hydroxyethyl-imidazolines. A preferred zwitterionic surfactant is known under the INCI name Cocamidopropyl betaine.

Preferred amphoteric surfactants are N-Alkylglycines, N-Alkylpropionic acids, N-Alkylaminobutyric acids, N-Alkyliminodipropionic acids, N-Hydroxyethyl-N-alkylamidopropylglycines, N-Alkyltaurines, N-Alkylsarcosines, 2-Alkylaminopropionic acids and Alkylaminoacetic acids. Particularly preferred amphoteric surfactants are N-Cocoalkylaminopropionate, as Cocoacylaminoethylaminopropionate and $C_{12}$-$C_{18}$-Acylsarcosine.

Preferred non-ionic surfactants are Alkyl polyglycosides and Alkylene oxide adducts to fatty alcohols and fatty acids with 2 to 30 mol ethylene oxide per mol fatty alcohol or fatty acid. Preparations with excellent properties are also obtained if they contain fatty acid esters of ethoxylated glycerol as non-ionic surfactants.

Preferred quaternary ammonium compounds are ammonium halides and the imidazolium compounds known by the INCI designations quaternium-27 and quaternium-83. Other cationic surfactants that can be used as contemplated herein are the quaternized protein hydrolysates. Stearamidopropyl dimethylamine, which is commercially available under the name Tegoamid® S 18, is a compound from the group of amidoamines that is particularly suitable for use in the present disclosure. Preferred esterquats are quaternized ester salts of fatty acids with triethanolamine, quaternized ester salts of fatty acids with diethanolalkylamines and quaternized ester salts of fatty acids with 1.2-dihydroxypropyl dialkylamines. The cationic surfactants are preferably present in the agents used as contemplated herein in proportions of 0.05 to 10 wt. %, based on the total agent.

The surfactants are preferably used in amounts of 0.1 to 45 wt. %, preferably 1 to 30 wt. % and very preferably 1 to 15 wt. %, based on the total amount of the agents.

Furthermore, the compositions as contemplated herein may additionally contain at least one solvent. Particularly well-suited solvents can be selected from the group of 1,2-propanediol, 1,3-propanediol, ethanol, isopropanol, diethylene glycol monoethyl ether, glycerol, 1,2-butylene glycol, dipropylene glycol, ethylene carbonate, propylene carbonate, 2-phenoxyethanol and benzyl alcohol.

The solvents are preferably used in proportions of 0.1 to 45 wt. %, preferably 1 to 30 wt. % and very preferably 1 to 15 wt. %, based on the total amount of the agents.

To adjust the desired viscosity or optimum flow behavior, the agents as contemplated herein can also additionally contain at least one polymeric thickener as a further optional component.

The following are some examples of typical polymeric thickeners for aqueous or waterborne systems:

Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/$C_{10-30}$ Alkyl Acrylate Cross polymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Cross polymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, Astragalus Gummifer Gum, Attapulgite, Avena Sativa (Oat) Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, Glycine Soja (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxypropyl Starch, Hydroxypropyl Starch Phosphate, Hydroxypropyl Xanthan Gum, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, Solanum Tuberosum (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, Triticum Vulgare (Wheat) Starch, Tromethamine Acrylates/Acrylonitrogens Copolymer, Tromethamine Magnesium Aluminum Silicate, Welan Gum, Xanthan Gum, Yeast Beta-Glucan, Yeast Polysaccharides, Zea Mays (Corn) Starch.

The polymeric thickener(s) are preferably used in proportions of from about 0.1 to about 45 wt. %, preferably from about 1 to about 30 wt. % and very preferably from about 1 to about 15 wt. %, based on the total amount of the agents.

Furthermore, the agents as contemplated herein may contain other active ingredients, auxiliaries and additives, for example non-ionic polymers (such as vinylpyrrolidinone/vinyl acrylate copolymers, polyvinylpyrrolidinone and vinylpyrrolidinone/vinyl acetate copolymers, polyethylene glycols and polysiloxanes); cationic polymers (such as quaternized cellulose ethers, polysiloxanes with quaternary groups, dimethyldiallyl ammonium chloride polymers, acrylamide-dimethyldiallyl ammonium chloride copolymers, diethyl sulfate quaternized dimethylamino-ethyl methacrylate-vinylpyrrolidinone copolymers, vinylpyrrolidinone-imidazolinium methochloride copolymers, and quaternized polyvinyl alcohol); zwitterionic and amphoteric polymers (such as acrylamidopropyl trimethylammonium chloride/acrylate copolymers and octylacrylamide/methyl methacrylate/t-butylaminoethyl methacrylate/2-hydroxypropyl methacrylate copolymers); anionic polymers (such as polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-t-butyl acrylamide terpolymers); other thickeners (such as agar-agar, guar-gum, alginates, gum arabic, karaya gum, locust bean gum, flaxseed gums, dextrans, cellulose derivatives, e.g. e.g., methyl cellulose, hydroxyalkyl cellulose and carboxymethyl cellulose, starch fractions and derivatives such as amylose, amylopectin and dextrins, clays such as bentonite, or fully synthetic hydrocolloids such as polyvinyl alcohol); structurants (such as glucose, maleic acid and lactic acid); hair-conditioning compounds (such as phospholipids, soy lecithin, egg lecithin and cephalins, and silicone oils); protein hydrolysates (in particular elastin, collagen, keratin, milk protein, soy protein and wheat protein hydrolysates, their condensation products with fatty acids, and quaternized protein hydrolysates); fiber structure-improving active ingredients (in particular mono-, di- and oligosaccharides such as glucose, galactose, fructose, fruit sugar and lactose); defoamers (such as silicones, preferably dimethicone); dyes for coloring the agent; antidandruff active ingredients (such as piroctone olamine, zinc omadine and climbazole); light stabilizers or UV blockers (in particular derivatized benzophenones, cinnamic acid derivatives and triazines); Active ingredients (such as panthenol, pantothenic acid, pantolactone, allantoin, pyrrolidinone carboxylic acids and their salts, and bisabolol); vitamins, provitamins and vitamin precursors (in particular those of groups A, B3, B5, B6, C, E, F and H); cholesterol; consistency enhancers (such as sugar esters, polyol esters or polyol alkyl ethers); fatty acid alkanolamides; Swelling and penetrating agents (such as glycerol, propylene glycol monoethyl ether, carbonates, hydrogen carbonates, guanidines, ureas, and primary, secondary and tertiary phosphates); opacifiers (such as latex, styrene/PVP and styrene/acrylamide copolymers); pearlescent agents (such as ethylene glycol mono- and distearate and PEG-3-distearate); pigments; perfume oils; blowing agents (such as propane-butane mixtures, N2O, dimethyl ether, $CO_2$ and air) and antioxidants.

The selection of these other substances will be made by the specialist according to the desired properties of the agents. With regard to further optional components as well as the quantities of these components used, explicit reference is made to the relevant manuals known to the skilled person, e.g. Kh. Schrader, Grundlagen und Rezepturen der Kosmetika, 2nd edition, Huthig Buch Verlag, Heidelberg, 1989, referred to.

Water Content in Agent

The agent described above is a ready-to-use agent that can be applied to the keratinous material. This ready-to-use agent preferably has a high-water content. It has been found that agents comprising—based on the total weight of the agent—about 50.0 to about 98.0 wt. %, preferably about 60.0 to about 90.0 wt. % and particularly preferably about 70.0 to about 90.0 wt. % of water are particularly suitable.

In a further explicitly quite particularly preferred embodiment, an agent as contemplated herein is wherein it comprises—based on the total weight of the agent—about 50.0 to about 98.0 wt. %, preferably about 60.0 to about 90.0 wt. % and particularly preferably about 70.0 to about 90.0 wt. % water.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:
(1) Application of a coloring agent to the keratinous material, wherein the coloring agent is an agent as disclosed in detail in the description of the first subject matter of the present disclosure,
(2) Exposure of the colorant to the keratinous material and
(3) Rinse out the dye.

In step (1) of the process as contemplated herein, the agent of the first present disclosure is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in very short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein is exemplified by:
(2) Exposure of the colorant to the keratinous material for a period of time ranging from 30 seconds to 15 minutes, preferably from 30 seconds to 10 minutes, and most preferably from 1 to 5 minutes.

Following the action of the application mixture on the keratin material, it is finally rinsed out in step (3) of the process.

Here, in one embodiment, the application mixture can be washed out with water only, i.e. without the aid of an after-treatment agent or a shampoo. The use of a post-treatment agent or conditioner after step (3) is also conceivable in principle.

Process for Dyeing Keratin Material, in which the Agent Ready for Use is First Prepared.

As previously described, the agent of the first subject present disclosure is an application-ready agent that is either provided directly to the user in its application-ready form, or is prepared by mixing various agents just prior to application.

In order to ensure a particularly fine distribution of the pigments, it has proved particularly preferable to prepare the ready-to-use agent shortly before application by mixing two or three different agents.

Accordingly, in a particularly preferred embodiment, the ready-to-use agent is prepared by mixing at least two different agents, the first of these two agents comprising a mixture of alkoxylated fatty acid ester (a3) and color-providing compound(s), in particular pigment(s) (a2). For example, the mixture of alkoxylated fatty acid ester (a3) and pigment(s) (a2) may represent a predispersion provided in the form of a concentrate. The second agent comprises at least one amino-functionalized silicone polymer (a1) and may, for example, be a water-comprising cosmetic carrier formulation. It is also as contemplated herein if the first agent comprising the mixture of alkoxylated fatty acid ester (a3) and pigment(s) (a2) is a water-comprising cosmetic carrier formulation and the second agent comprising the amino-functionalized silicone polymer (a1) is in the form of a concentrate. The two aforementioned agents are then shaken or stirred together to prepare the ready-to-use agent.

Furthermore, it is as contemplated herein that ready-to-use colorants are prepared by mixing three agents previously prepared separately, the first agent being a mixture or predispersion of alkoxylated fatty acid ester (a3) and pigment(s) (a2), the second mixture comprises an amino-functionalized silicone polymer (a1) and may, for example, be in the form of a concentrate, and the third agent is a water-comprising cosmetic carrier formulation which preferably comprises at least one alkoxylated alkanol (a4).

A further subject of the present application is therefore a method for coloring keratinous material, in particular human hair, comprising the following steps:
(1) Providing an agent (I), wherein the agent (I) comprises:
    (a2) at least one pigment and
    (a3) at least one addition product of $C_1$-$C_6$ alkylene oxide(s) to the esters of $C_{12}$-$C_{30}$ fatty acids and $C_1$-$C_{12}$ aromatic alcohols.
(2) Providing an agent (II), wherein the agent (II) comprises:
    (a1) at least one amino-functionalized silicone polymer, and
(3) Prepare an application mixture by mixing the agent (I) with the agent (II),
(4) Apply the application mixture prepared in step (3) to the keratinous material,
(5) Exposure of the application mixture applied in step (4) to the keratinous material; and
(6) Rinse the application mixture with water,
wherein the ingredients (a1), (a2) and (a3) have already been disclosed in detail in the description of the first subject matter of the present disclosure.

In the context of this embodiment, the optionally additionally applicable alkoxylated alkanols (a4) may, for example, be present in the agent (I) and/or in the agent (II).

Depending on the selected pH, the amino silicone (a3) has in some cases shown reduced storage stability in aqueous environments. In these cases, it may be advantageous to also use the
amino functionalized silicone polymer (a3) in a separate agent and to mix both the ingredients (a1) and (a2) and the amino silicone (a3) with a base formulation only shortly before use. In this case, at least three different agents are mixed together to produce the ready-to-use colorant.

Particularly preferred, therefore, is a process for dyeing keratinous material, in particular human hair, comprising the following steps:

(1) Providing an agent (I), wherein the agent (I) comprises:
   (a2) at least one pigment and
   (a3) at least one addition product of $C_1$-$C_6$ alkylene oxide(s) to the esters of $C_{12}$-$C_{30}$ fatty acids and $C_1$-$C_{12}$ aromatic alcohols.
(2) Providing an agent (II), wherein the agent (II) comprises:
   (a1) at least one amino-functionalized silicone polymer, and
(3) Providing an agent (III), wherein the agent (III) comprises:
   a4) at least one Addition products of $C_1$-$C_6$ alkylene oxide(s) to aliphatic $C_1$-$C_{24}$ alkanols (a4)

(4) Prepare an application mixture by mixing the agent (I) with the agent (II) and optionally with the agent (III),
(5) Apply the application mixture prepared in step (4) to the keratinous material,
(6) Exposure of the application mixture applied in step (5) to the keratinous material; and
(7) Rinse out the application mixture,
wherein the ingredients (a1), (a2), (a3) and (a4) have already been disclosed in detail in the description of the first subject matter of the present disclosure.

In the context of this embodiment, the agent (I) preferably represents a predispersion of the pigments (a2) in the alkoxylated fatty acid ester(s) (a3), which may be in the form of a concentrate, for example. The agent (II) is preferably also a concentrate comprising the amino-functionalized silicone polymer(s) (a1).

Before application, the two agents or concentrates (I) and (II) are then mixed with the carrier formulation (III). In this embodiment, the cosmetic carrier formulation or agent (III), comprises the alkoxylated alkanols (a4).

The order of mixing is arbitrary. Thus, agents (I) and (II) can first be mixed with one another, whereupon this mixture is then mixed with agent (III). Likewise, it is conceivable to first mix agents (II) and (III) and then mix this mixture with agent (I). Also, all three agents (I), (II) and (III) can be added together and then mixed by shaking or stirring first.

The carrier formulation comprises water and preferably has a high-water content. The optionally applicable further ingredients of the first present disclosure may also be included in this carrier formulation.

Concerning the further preferred embodiments of the methods as contemplated herein, mutatis mutandis what has been said about the agent as contemplated herein applies.

Examples

1. Formulations

The following formulations were prepared (all data in wt. % unless otherwise stated):

|  |  | Example 1 | Example 2 | Example 3 | Example 4 |
|---|---|---|---|---|---|
| Cream Base | Cetyl alcohol | 3.57 | 3.57 | 3.57 | 3.57 |
|  | Stearyl alcohol | 1.98 | 1.98 | 1.98 | 1.98 |
|  | Paraffinum Liquidum | 2.08 | 2.08 | 2.08 | 2.08 |
|  | Ceteareth-30 | 1.19 | 1.19 | 1.19 | 1.19 |
|  | Ceteareth-100 | 0.59 | 0.59 | 0.59 | 0.59 |
|  | Glyceryl stearate | 0.59 | 0.59 | 0.59 | 0.59 |
|  | Water, dist. | 61.67 | 61.67 | 61.67 | 61.67 |
|  | Potassium dihydrogen phosphate | 0.35 | 0.35 | 0.35 | 0.35 |
|  | Disodium hydrogen phosphate (dihydrate) | 0.72 | 0.72 | 0.72 | 0.72 |
|  | Phenoxyethanol | 0.89 | 0.89 | 0.89 | 0.89 |
| Predispersion | Unipure Red LC 3079 | 0.50 | — | 0.50 | 0.38 |
|  | PPG-3 Benzyl Ether Myristate Crodamol STS-LQ-(MH) | 4.95 | — | 2.00 | 1.50 |
| Additives | Water, demineralized | 19.92 | 21.87 | 21.87 | 22.74 |
|  | PPG-3 Benzyl Ether Myristate Crodamol STS-LQ-(MH) | — | 3.00 | — | — |
|  | Unipure Red LC 3079 | — | 0.50 | — | — |
|  | PPG-14 Butyl ether UCON FLUID AP | — | — | 1.00 | 1.00 |
| Activator | DOWSIL AP-8568 Amino Fluid, Aminosilicone | 1.00 | 1.00 | 1.00 | 0.75 |

A cream base was first prepared from the specified ingredients. The specified additives were then added to this cream base.

In the formulation of Example 1, only a proportion of water was added to the cream base as an additive.

In the formulation of Example 2, water, PPG-3 benzyl ether myristate (a3) and the pigment Unipure Red LC 3079 (a2) were successively incorporated into the cream base as additives.

In the formulations of Examples 3 and 4, water and PPG-14 butyl ether (a4) were added to the cream base as additives.

In example formulations 1, 3 and 4, the pigment Unipure Red LC 3079 (a2) and PPG-3 benzyl ether myristate (a3) were then each mixed separately so that this mixture was in the form of a predispersion. This predispersion was then incorporated into the cream base.

In the last step, the amino silicone DOWSIL AP-8568 Amino Fluid (a1) was added to all four example formulations 1 to 4.

2. Application

Hair strands (Kerling Euronaturhaar white) were first measured colorimetrically using a colorimeter from the company Datacolor, type Spectraflash 450.

The formulations of Examples 1 to 4 were applied as agents for coloring hair as follows: After preparation, the respective agent was applied to hair strands (Kerling, Euronatural hair white, liquor ratio: 1 g agent (E1) per g hair strand). The agent was left to act for three minutes. Subsequently, the hair strand was thoroughly washed (1 minute) with water, dried and then colorimetrically measured with a colorimeter from Datacolor, type Spectraflash 450.

The ΔE value used to assess the color intensity is derived from the L*a*b* colorimetric values measured on the respective strand part as follows:

$$\Delta E = [(L_i - L_0)^2 + (a_i - a_0)^2 + (b_i - b_0)^2]^{1/2}$$

L0, a0 and b0=Measured values of the strand before dyeing $L_i$, $a_i$ and $b_i$=Measured values of the strand after dyeing The greater this ΔE value, the higher (=better) is the intensity of the coloration The dyed hair strands were evaluated in terms of their feel by 10 trained individuals each. For hair feel, scores from 1 to 6 were distributed (1: very poor hair feel (rough, brittle, dull), 6: very good hair feel (smooth, soft, well-groomed)).

The dyed hair strands were also evaluated in terms of their rub fastness. For the evaluation of the rub fastness, hair strands were subjected to a standardized mechanical abrasion and then measured again colorimetrically. The ΔE value used to assess rub fastness is derived from the L*a*b* colorimetric values measured on the respective strand part as follows:

$$\Delta E = [(L_i - L_0)^2 + (a_i - a_0)^2 + (b_i - b_0)^2]^{1/2}$$

$L_0$, $a_0$ and $b_0$=Measured values of the strand after dyeing
$L_i$, $a_i$ and $b_i$=Measured values of the strand after dyeing and after mechanical stress The greater this ΔE value, the higher the color shift caused by the abrasion, i.e. the poorer the rub fastness.

After dyeing and drying, each strand was subjected to 3 manual hair washes. For each hair wash, the strand was dampened, then a commercial shampoo (Schwarzkopf, Schauma 7 herbs) was massaged into the strand for 25 seconds (0.25 g of shampoo per gram of hair). The strand was then washed with lukewarm tap water for 30 seconds and dried. After completion of the 3 hair washes, each strand was colorimetrically measured again.

The ΔE value used for the assessment of wash fastness is derived from the measured L*a*b* colorimetric values as follows:

$$\Delta E = [(L_i - L_0)^2 + (a_i - a_0)^2 + (b_i - b_0)^2]^{1/2}$$

$L_0$, $a_0$ and $b_0$=Measured values of the dyed strand after dyeing and before washing $L_i$, $a_i$ and $b_i$=Measured values of the dyed strand after 3 hair washes The greater this ΔE value, the higher the color shift caused by the wash, i.e. the poorer the wash fastness.

The following results were obtained:

|  | Example 1 | Example 2 | Example 3 | Example 4 |
|---|---|---|---|---|
| Color intensity, ΔE value (before dyeing – after dyeing) | 67 | 69 | 69 | 67 |
| Wash fastness, ΔE-value (before washing – after 3 hair washes). | 14 | 19 | 14 | 11 |
| Rubbing fastness, ΔE-value (before abrasion – after abrasion) | 11 | 18 | 8 | 7 |
| Hair feel/hair grip | 2 | 3 | 2.2 | 2.2 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous material, comprising:
   (a1) at least one amino-functionalized silicone polymer;
   (a2) at least one color-imparting compound;
   (a3) at least one addition product of $C_1$-$C_6$ alkylene oxide(s) to the esters of $C_{12}$-$C_{30}$ fatty acids and $C_1$-$C_{12}$ aromatic alcohols; and
   (a4) at least one addition product of $C_1$-$C_6$ alkylene oxide(s) to aliphatic $C_1$-$C_{24}$ alkanols.

2. The agent of claim 1, wherein the at least one amino-functionalized silicone polymer (a1) comprises at least one secondary amino group.

3. The agent of claim 1, wherein the at least one amino-functionalized silicone polymer (a1) comprises at least one structural unit of the formula (Si amino):

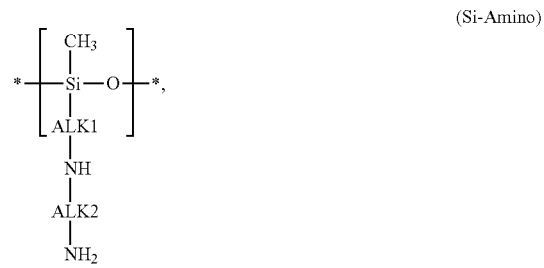

(Si-Amino)

where each ALK1 and ALK2 independently represents a linear or branched $C_1$-$C_{20}$ divalent alkylene group.

4. The agent of claim 1, wherein the at least one amino-functionalized silicone polymer (a1) comprises structural units of the formula (Si-I) and of the formula (Si-II):

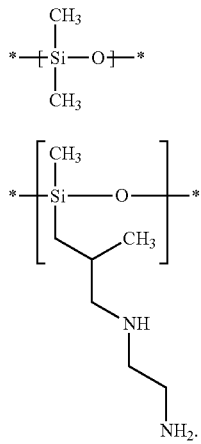

5. The agent of claim 1, wherein the one or more amino-functionalized silicone polymers (a1) is present in a total amount of from about 0.1 to about 8.0 wt. %, based on the total weight of the agent.

6. The agent of claim 1, wherein the at least one colorant compound (a2) is selected from the group of pigments, direct dyes, photochromic dyes, thermochromic dyes, and combinations thereof.

7. The agent of claim 1, wherein the at least one colorant compound (a2) comprises an inorganic pigment selected from the group of colored metal oxides, metal hydroxides, metal oxide hydrates, silicates, metal sulfides, complex metal cyanides, metal sulfates, bronze pigments, colored mica- or mica-based pigments coated with at least one metal oxide and/or a metal oxychloride, and combinations thereof.

8. The agent of claim 1, wherein the at least one coloring compound (a2) comprises an organic pigment selected from the group of carmine, quinacridone, phthalocyanine, sorghum, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470, and combinations thereof.

9. The agent of claim 1, wherein the one or more pigments (a2) is present in a total amount of from about 0.01 to about 10.0 wt. %, based on the total weight of the agent.

10. The agent of claim 1, wherein the at least one addition product (a3) comprises at least one addition product of $C_1$-$C_6$ alkylene oxide(s) to an ester obtained by esterification of a $C_{12}$-$C_{24}$ fatty acid with a $C_1$-$C_{12}$ aromatic alcohol selected from the group of benzyl alcohol, phenol, 2-phenylethyl alcohol, and 2-phenoxyethanol.

11. The agent of claim 1, wherein the at least one addition product (a3) comprises at least one alkoxylated fatty acid ester of the general formula (AFE-I):

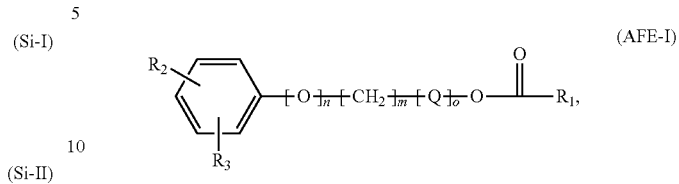

where
$R_1$ represents a saturated or unsaturated $C_{11}$-$C_{29}$ alkyl group;
$R_2$ and $R_3$ each independently represent a hydrogen atom, a $C_1$-$C_6$ alkyl group, a hydroxy group, or a $C_1$-$C_6$ alkoxy group;
n is 0 or 1;
m is an integer of from 0 to 6, with the proviso that if m is 0, then n is also 0;
o is an integer of from 1 to 60; and
each Q represents a structural unit selected from —O—$CH_2$—$CH_2$—, —O—CH($CH_3$)—$CH_2$— and —O—$CH_2$—CH($CH_3$)—.

12. The agent of claim 11, wherein:
$R_1$ represents a saturated or unsaturated $C_{11}$-$C_{29}$ alkyl group;
$R_2$ and $R_3$ are each a hydrogen atom;
n is 0;
m is 1;
o is an integer from 1 to 30; and
each Q is a structural unit selected from —O—CH($CH_3$)—$CH_2$— and —O—$CH_2$—CH($CH_3$)—.

13. The agent of claim 1, wherein the at least one addition product (a3) is present in a total amount of from about 0.1 to about 20.0 wt. %, based on the total weight of the agent.

14. The agent of claim 1, wherein the at least one addition product (a4) comprises at least one addition product of $C_1$-$C_6$ alkylene oxide(s) to aliphatic $C_1$-$C_{24}$ alkanols of the formula (AA-I):

where
$R_4$ represents a saturated or unsaturated $C_1$-$C_{24}$ alkyl group;
P represents a structural unit selected from —O—$CH_2$—$CH_2$—, —O—CH($CH_3$)—$CH_2$—, and —O—$CH_2$—CH($CH_3$)—; and
s is an integer of from 1 to 60.

15. The agent of claim 1, wherein the at least one addition product (a4) is present in a total amount of from about 0.1 to about 20.0 wt. %, based on the total weight of the agent.

16. The agent of claim 1, further comprising water and having a pH of from about 3.8 to about 11.5.

17. A method for dyeing keratinous material, comprising:
(1) applying the agent of claim 1 to keratinous material;
(2) exposing the agent to the keratinous material; and
(3) rinsing the keratinous material to remove the agent therefrom.

* * * * *

UNITED STATES PATENT AND TRADEMARK OFFICE
CERTIFICATE OF CORRECTION

PATENT NO. : 12,318,470 B2
APPLICATION NO. : 18/251128
DATED : June 3, 2025
INVENTOR(S) : Constanze Kruck et al.

It is certified that error appears in the above-identified patent and that said Letters Patent is hereby corrected as shown below:

In the Specification

Column 22, Line 9 change "represents an integer from 1 to 60," to --o represents an integer from 1 to 60--.
Column 22, Line 43 change "represents an integer from 1 to 60," to --o represents an integer from 1 to 60--.
Column 23, Line 22 change "represents an integer from 1 to 60," to --o represents an integer from 1 to 60--.
Column 23, Line 60 change "is an integer from 1 to 30," to --o represents an integer from 1 to 60--.
Column 24, Line 15 change "is an integer from 1 to 30," to --o is an integer from 1 to 30--.
Column 24, Line 33 change "is an integer from 1 to 30," to --o is an integer from 1 to 30--.
Column 24, Line 53 change "is an integer from 1 to 30," to --o is an integer from 1 to 30--.
Column 29, Line 33 change "omithine" to --ornithine--.

Signed and Sealed this
Sixteenth Day of September, 2025

Coke Morgan Stewart
*Acting Director of the United States Patent and Trademark Office*